United States Patent
Hagiwara

(10) Patent No.: US 10,281,446 B2
(45) Date of Patent: May 7, 2019

(54) ENGINE CONTROL DEVICE

(71) Applicant: FUJITSU TEN LIMITED, Kobe-shi, Hyogo (JP)

(72) Inventor: Masatoshi Hagiwara, Kobe (JP)

(73) Assignee: FUJITSU TEN Limited, Kobe-shi (JP)

( * ) Notice: Subject to any disclaimer, the term of this patent is extended or adjusted under 35 U.S.C. 154(b) by 0 days.

(21) Appl. No.: 15/667,048

(22) Filed: Aug. 2, 2017

(65) Prior Publication Data

US 2018/0136183 A1 May 17, 2018

(30) Foreign Application Priority Data

Nov. 16, 2016 (JP) ................................ 2016-223556

(51) Int. Cl.
| | |
|---|---|
| F02B 47/08 | (2006.01) |
| G01N 33/00 | (2006.01) |
| F02M 26/46 | (2016.01) |
| F02D 41/00 | (2006.01) |
| H05B 3/06 | (2006.01) |
| F02D 41/12 | (2006.01) |

(Continued)

(52) U.S. Cl.
CPC ..... *G01N 33/0073* (2013.01); *F02D 41/0052* (2013.01); *F02D 41/0077* (2013.01); *F02D 41/123* (2013.01); *F02D 41/144* (2013.01); *F02D 41/1454* (2013.01); *F02D 41/1494* (2013.01); *F02D 41/2464* (2013.01); *F02M 26/46* (2016.02); *G01N 33/0036* (2013.01); *H05B 1/0244* (2013.01); *H05B 3/06* (2013.01); *F02D 2200/602* (2013.01); *Y02T 10/47* (2013.01)

(58) Field of Classification Search
CPC ......... F02D 41/1454; F02D 2041/2048; F02D 41/146; F02D 41/1494; F02D 2041/2027; G05D 23/1919; G05D 23/24; G05D 23/19
USPC ............ 123/568.11, 566.21, 568.22, 568.23, 123/568.31
See application file for complete search history.

(56) References Cited

U.S. PATENT DOCUMENTS

| | | | |
|---|---|---|---|
| 2002/0014103 A1* | 2/2002 | Matsubara ............ | F02D 41/144 73/1.06 |
| 2012/0031077 A1* | 2/2012 | Aoki ..................... | F01N 13/008 60/276 |

(Continued)

FOREIGN PATENT DOCUMENTS

JP        2010-203281 A        9/2010

*Primary Examiner* — John Kwon
(74) *Attorney, Agent, or Firm* — Oliff PLC

(57) ABSTRACT

An engine control device of a vehicle engine includes a processor that detects an operation state of the engine and controls an output of a heater which heats an intake air oxygen concentration sensor detecting oxygen concentration of intake air of the engine. The intake air includes a portion of exhaust gas recirculated to an intake passage of the engine as EGR gas. The processor controls the output of the heater, according to a detected operation state of the engine, so that the intake air oxygen concentration sensor enters one of (i) an active state where a temperature of the intake air oxygen concentration sensor becomes greater than or equal to an activation temperature, (ii) a semi-active state where the sensor temperature is lower than the activation temperature and higher than an inactivation temperature, and (iii) an inactive state where the sensor temperature is lower than the inactivation temperature.

5 Claims, 6 Drawing Sheets

(51) Int. Cl.
    *F02D 41/14*     (2006.01)
    *F02D 41/24*     (2006.01)
    *H05B 1/02*     (2006.01)

(56) References Cited

U.S. PATENT DOCUMENTS

| | | | |
|---|---|---|---|
| 2013/0131997 A1* | 5/2013 | Inagaki | G01M 15/042 |
| | | | 702/24 |
| 2013/0133399 A1* | 5/2013 | Hibino | F02D 41/1494 |
| | | | 73/23.31 |
| 2015/0068278 A1* | 3/2015 | Yazawa | G01M 15/104 |
| | | | 73/23.32 |
| 2016/0274073 A1* | 9/2016 | Hakeem | G01N 30/7206 |
| 2017/0205326 A1* | 7/2017 | Kato | G01N 27/4067 |

* cited by examiner

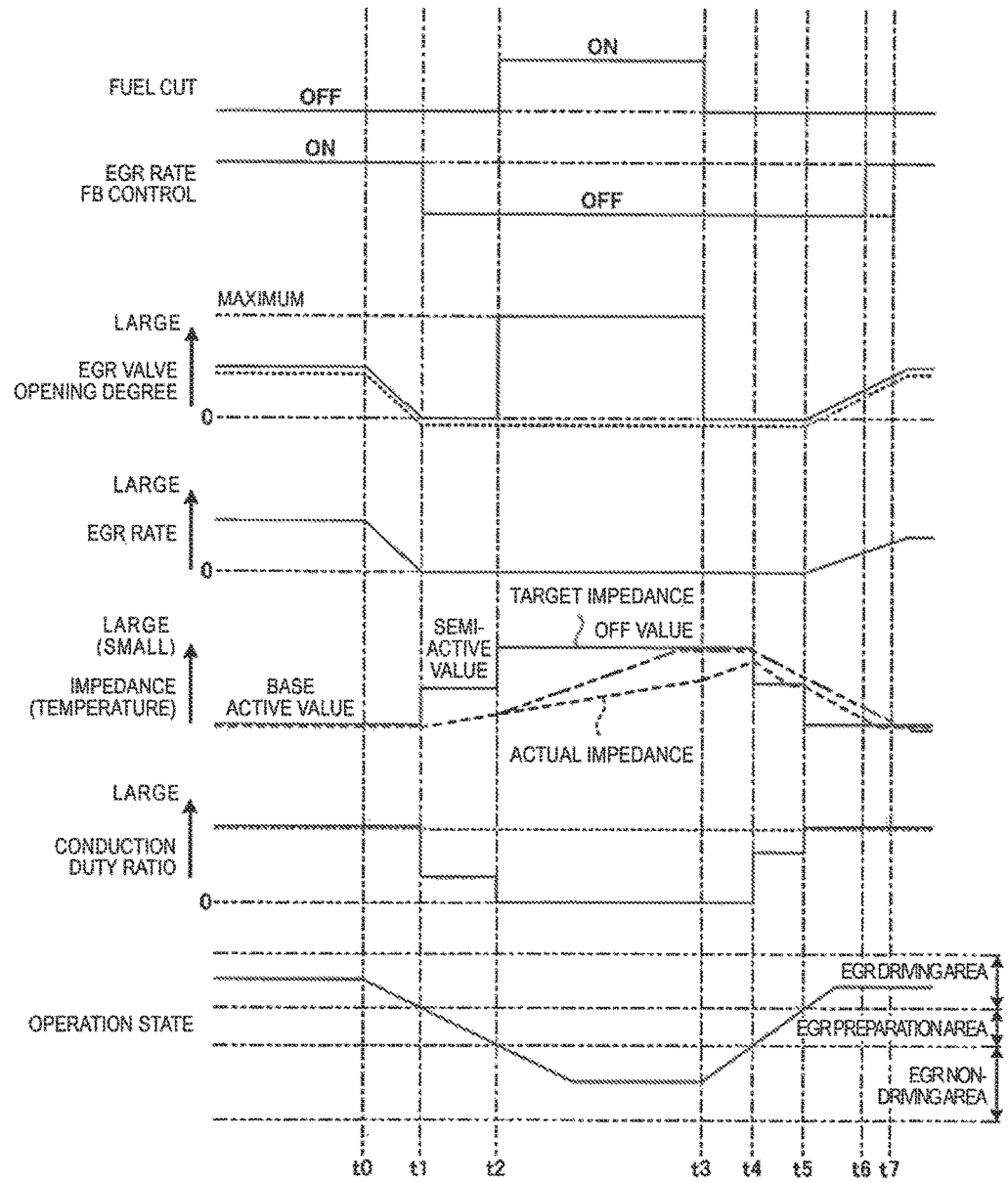

ENGINE CONTROL DEVICE

BACKGROUND OF THE INVENTION

Field of the Invention

The present invention relates to a technology for controlling an engine.

Description of the Background Art

In the related art, an engine control device in which an oxygen concentration sensor is arranged in an intake passage in order to detect oxygen concentration of intake air in a case where exhaust gas recirculation (EGR) gas is recirculated in an internal combustion engine in which EGR gas is recirculated into an intake passage (for example, JP-A-2010-203281).

In order to accurately detect oxygen concentration of intake air by an oxygen concentration sensor, the oxygen concentration sensor needs to enter a state of being in a high activation temperature (for example, 700 degrees). For that reason, a heater is embedded in the oxygen concentration sensor and the oxygen concentration sensor is heated by the heater.

However, when the oxygen concentration sensor is heated by the heater at all times in order to maintain the oxygen concentration sensor at an activation temperature, power consumption of the heater is increased.

SUMMARY OF THE INVENTION

According to an aspect of the present invention, there is provided an engine control device that includes a processor. The processor detects an operation state of an engine, and controls an output of a heater which heats an intake air oxygen concentration sensor detecting oxygen concentration of intake air, which includes a portion of exhaust gas recirculated to an intake passage as EGR gas. The processor controls the output of the heater, according to the operation state of the engine detected by the processor, so that the intake air oxygen concentration sensor enters one of (i) an active state where a temperature of the intake air oxygen concentration sensor becomes greater than or equal to an activation temperature, (ii) a semi-active state where the temperature of the intake air oxygen concentration sensor is lower than the activation temperature and higher than an inactivation temperature, and (iii) an inactive state where the temperature is lower than the inactivation temperature.

With this, it is possible to reduce power consumption of the heater.

According to another aspect of the present invention, the processor controls the output of the heater so that the intake air oxygen concentration sensor enters the semi-active state, in a case where the operation state of the engine is in an EGR preparation area which is a transition area between an EGR driving area, in which the EGR gas is recirculated to the intake passage, and an EGR non-driving area.

With this, in a case where the operation state of the engine transits from the EGR preparation area to the EGR driving area, it is possible to put the intake air oxygen concentration sensor into the active state in a short time and it is possible to quickly adjust an EGR rate based on oxygen concentration detected accurately by the intake air oxygen concentration sensor.

Therefore, an object of the present inventions is to provide a technique for reducing power consumption of the heater.

These and other objects, features, aspects and advantages of the present invention will become more apparent from the following detailed description of the present invention when taken in conjunction with the accompanying drawings.

BRIEF DESCRIPTION OF THE DRAWINGS

FIG. 6 is a time chart for explaining output control of the electric heater.

DESCRIPTION OF THE EMBODIMENTS

In the following, an engine control device disclosed in the present application will be described with reference to the accompanying drawings. The present invention is not limited to the embodiments to be described in the following.

1. Outline of Output Control of Electric Heater

An engine which is a control target of an engine control device (in the following, referred to as an engine control unit (ECU)) according to an embodiment includes an EGR device which recirculates a portion of exhaust gas as EGR gas in a case where an operation state of an engine is in an EGR driving area.

In a case where the operation state of the engine is in the EGR driving area in which EGR gas is recirculated, the ECU controls an opening degree of an EGR valve based on oxygen concentration detected by an intake air oxygen concentration sensor to adjust an EGR rate which is a ratio of EGR gas included in intake air.

When a temperature of a sensor element does not enter an active state greater than or equal to an activation temperature, the intake air oxygen concentration sensor is unable to accurately detect oxygen concentration. For that reason, an electric heater for heating is embedded in the intake air oxygen concentration sensor. The activation temperature is a preset temperature, a lower limit temperature at which the intake air oxygen concentration sensor enters the active state, and is, for example, 700 degrees.

When the intake air oxygen concentration sensor is heated by the electric heater, electric power is consumed by the electric heater. For that reason, when the intake air oxygen concentration sensor is heated at all time by the electric heater, power consumption of the electric heater is increased.

Figure 1:
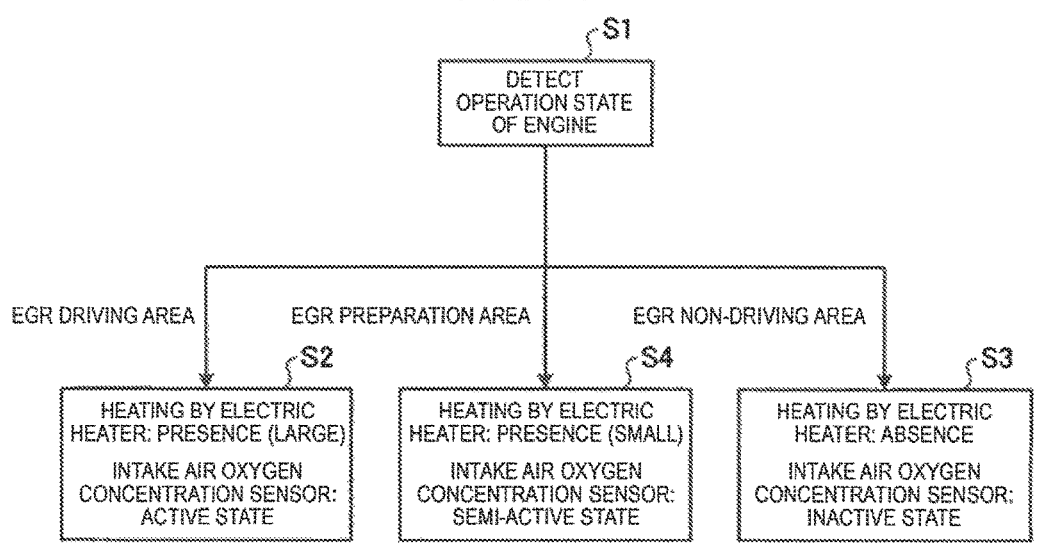
FIG. 1 is a diagram for explaining an outline of output control of an electric heater according to an embodiment.

The ECU according to the embodiment performs output control of the electric heater in order to reduce power consumption of the electric heater. Description will be on an outline of output control of the electric heater according to the embodiment using FIG. 1. FIG. 1 is a diagram for explaining an outline of output control of the electric heater.

The ECU detects an operation state of an engine (S1) and heats the intake air oxygen concentration sensor by the electric heater so that the intake air oxygen concentration sensor enters the active state, in a case where the operation state of the engine is in the EGR driving area (S2).

The EGR rate does not need to be adjusted in a case where the operation state of the engine is in an EGR non-driving area in which EGR gas is not recirculated and thus, it is possible to put the intake air oxygen concentration sensor into an inactive state in which the temperature of the sensor element becomes equal to or lower than the inactivation temperature lower than an activation temperature. For that reason, the ECU turns the electric heater to OFF to put the intake air oxygen concentration sensor into the inactive state without performing heating by the electric heater (S3). The inactivation temperature is a preset temperature and is, for example, 600 degrees.

In a case where the operation state of the engine is in an EGR preparation area provided between the EGR driving area and the EGR non-driving area, the ECU heats the intake air oxygen concentration sensor by the electric heater so that the intake air oxygen concentration sensor enters the semi-active state (S4).

The EGR preparation area is an area of a stage before the operation state of the engine transits to the EGR driving area. In a case where the operation state of the engine is in the EGR preparation area, EGR gas is not recirculated.

The semi-active state is a state in which the temperature of the sensor element is lower than the activation temperature and higher than the inactivation temperature. For example, in a case where the temperature of the sensor element is higher than 600 degrees and lower than 700 degrees, the intake air oxygen concentration sensor enters the semi-active state.

The temperature of the sensor element in the semi-active state is lower than the temperature of the sensor element in the active state and thus, a heating amount of the electric heater needed to enter the semi-active state is less than the heating amount of the electric heater needed to enter the active state. That is, the intake air oxygen concentration sensor is put into the semi-active state so as to make it possible to reduce power consumption of the electric heater than a case of maintaining the intake air oxygen concentration sensor in the active state.

In a case where the intake air oxygen concentration sensor is in the semi-active state, the intake air oxygen concentration sensor is heated by the electric heater so as to make it possible to cause the intake air oxygen concentration sensor to transit to the active state in a short time. For that reason, in a case where the operation state of the engine transits from the EGR preparation area to the EGR driving area, it is possible to put the intake air oxygen concentration sensor into the active state in a short time and to quickly adjust the EGR rate based on oxygen concentration detected accurately by the intake air oxygen concentration sensor.

As described above, in the embodiment, the intake air oxygen concentration sensor controls the output of the electric heater to enter any of the active state where the temperature of the intake air oxygen concentration sensor is greater than or equal to an activation temperature, the semi-active state where the temperature is lower than that in the active state, and the inactive state where the temperature is lower than that in the semi-active state according to the operation state of the engine. With this, it is possible to reduce power consumption of the electric heater compared to a case where the intake air oxygen concentration sensor is heated by the electric heater at all times.

In the following, details of a configuration of the engine and output control of the electric heater will be described. In the following, the temperature of the sensor element may be described as a temperature of the intake air oxygen concentration sensor.

2. Outline of Entire Configuration

Figure 2:
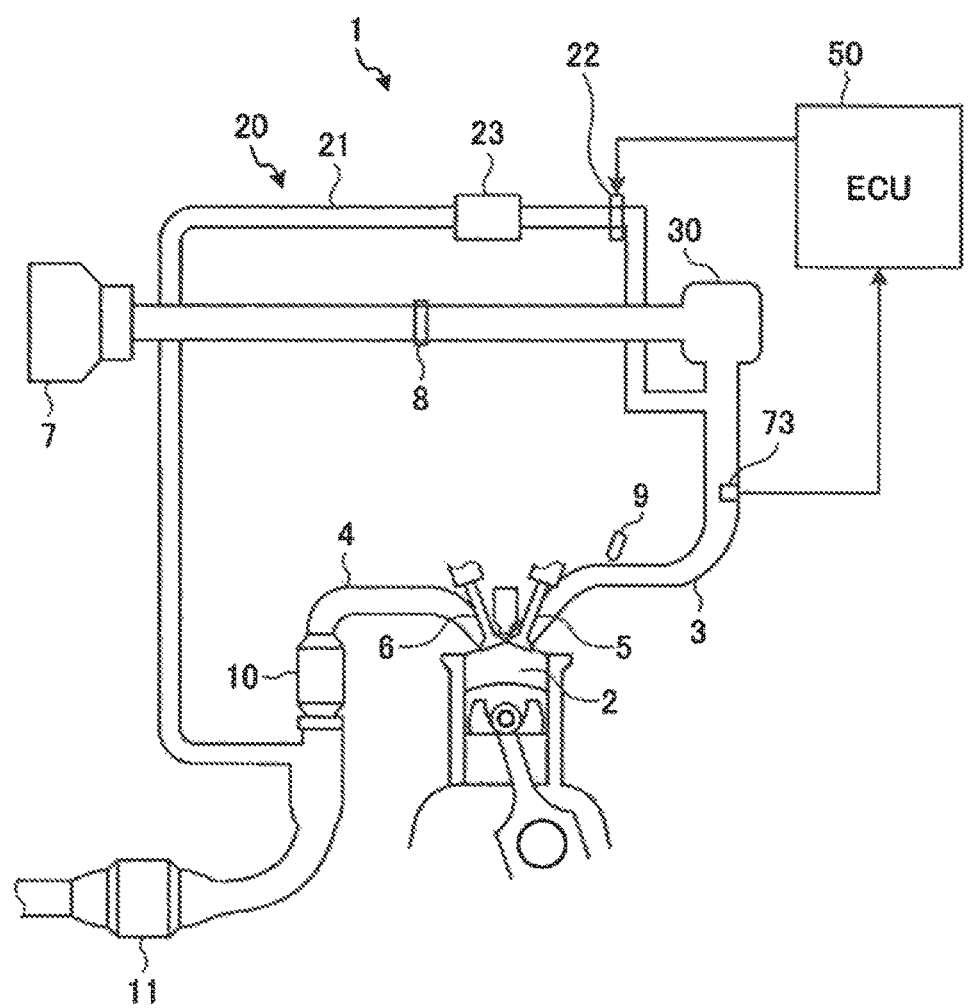
FIG. 2 is a diagram illustrating an outline of an internal combustion engine according to the embodiment.

FIG. 2 is a diagram illustrating an outline of an engine 1 according to the embodiment of the present invention. The engine 1 illustrated in FIG. 2 is, for example, an internal combustion engine using gasoline as fuel and is equipped in an automobile. The engine 1 includes an EGR device 20. In the engine 1, various control such as combustion control is performed by an ECU 50. Although the engine 1 of a single cylinder is illustrated in FIG. 2, the engine 1 of multiple cylinders may be used without being limited thereto.

A cylinder 2 of the engine 1 of FIG. 2 is connected with an intake pipe 3 and an exhaust pipe 4. An intake passage is formed of the intake pipe 3 and an exhaust passage is formed of the exhaust pipe 4.

An intake valve 5 is provided on the intake pipe 3. External air (fresh air) flows into the intake pipe 3 from an intake port 7 provided with an air cleaner (not illustrated). A surge tank 30 is provided on the intake pipe 3. An electronic control type throttle valve 8 is provided on the intake pipe 3 between the air cleaner and the surge tank 30.

The intake pipe 3 between the surge tank 30 and the cylinder 2 is connected with an EGR gas recirculation pipe 21. An intake air oxygen concentration sensor 73 and an injector 9 are provided on a portion, which is between a point connected with the EGR gas recirculation pipe 21 and the cylinder 2, of the intake pipe 3. The injector 9 is provided on a portion of the intake pipe 3 of the cylinder 2 side to be closer thereto than the intake air oxygen concentration sensor 73, and fuel is injected into the intake pipe 3.

An exhaust valve 6 is provided on the exhaust pipe 4. A ternary catalyst device 10 and an NOx occlusion and reduction type ternary catalyst device 11 are provided on the exhaust pipe 4. The ternary catalyst device 10 is provided on a portion of the exhaust pipe 4 of the cylinder 2 side to be closer thereto than the NOx occlusion and reduction type ternary catalyst device 11.

The ternary catalyst device 10 and the NOx occlusion and reduction type ternary catalyst device 11 are devices that use a catalyst to purify harmful components contained in exhaust gas. The harmful components contained in exhaust gas of an automobile include mainly hydrocarbon, carbon monoxide, nitrogen oxide (NOx), and the like.

In the ternary catalyst device 10 or the NOx occlusion and reduction type ternary catalyst device 11, it is possible to simultaneously remove the harmful components by oxidizing and reducing by catalysts, for example, platinum, palladium, and rhodium.

The exhaust pipe 4 between the ternary catalyst device 10 and the NOx occlusion and reduction type ternary catalyst device 11 is connected with the EGR gas recirculation pipe 21.

The EGR device 20 includes the EGR gas recirculation pipe 21, an EGR valve 22, and an EGR cooler 23.

The EGR gas recirculation pipe 21 connects the intake pipe 3 and the exhaust pipe 4 and recirculates a portion of exhaust gas flowing in the exhaust pipe 4 to the intake pipe 3 as EGR gas. An EGR gas passage is formed of the EGR gas recirculation pipe 21. An end portion of one side of the EGR gas recirculation pipe 21 is connected to the exhaust pipe 4 between the ternary catalyst device 10 and the NOx occlusion and reduction type ternary catalyst device 11 and an end portion of the other side thereof is connected to the intake pipe 3 between the surge tank 30 and the cylinder 2.

The EGR valve 22 is provided on the EGR gas recirculation pipe 21. The EGR valve 22 is a solenoid valve, is operated by allowing the current to a linear solenoid (not illustrated) to be controlled based on a signal from the ECU 50, and the opening degree of the EGR valve 22 is controlled. The opening degree of the EGR valve 22 is controlled so as to control a recirculation amount of EGR gas. When the opening degree of the EGR valve 22 becomes large, the recirculation amount of EGR gas is increased.

The EGR cooler 23 is provided on a portion of the EGR gas recirculation pipe 21 of the exhaust pipe 4 side to be closer thereto than the EGR valve 22. The EGR cooler 23 cools down EGR gas using circulated cooling water. It is possible to control a flow rate of cooling water by, for example, a cooling water pump (not illustrated) and control a temperature of EGR gas.

3. Outline of ECU 50

Figure 3:
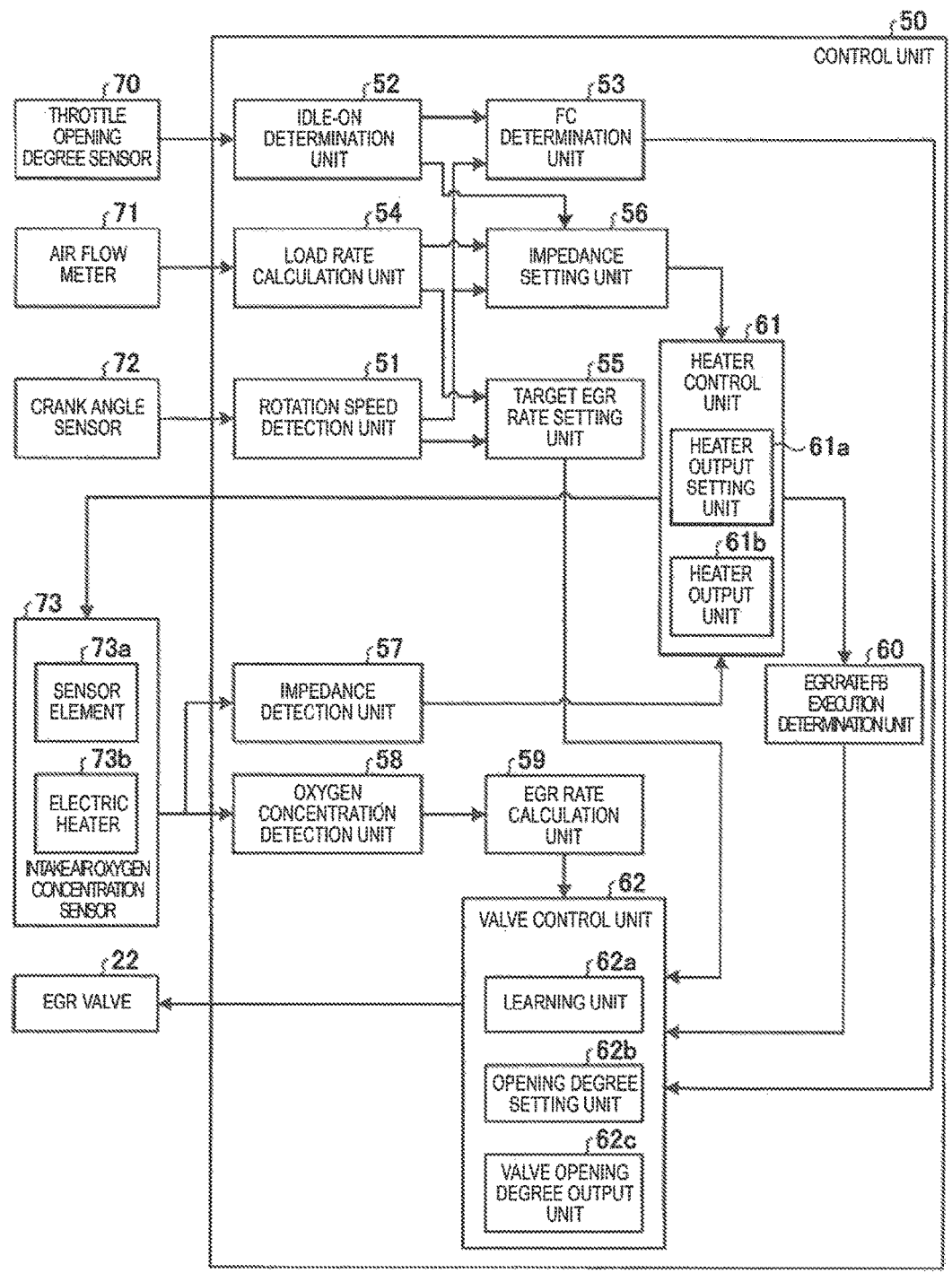
FIG. 3 is a block diagram illustrating an ECU according to the embodiment.

Next, description will be made on the ECU 50 using FIG. 3. FIG. 3 is a block diagram illustrating the ECU 50 according to the embodiment.

The ECU 50 controls a conduction duty ratio which is an output of an electric heater 73b and an opening degree of the EGR valve 22 based on signals from a throttle opening degree sensor 70, an air flow meter 71, a crank angle sensor 72, and the intake air oxygen concentration sensor 73.

The throttle opening degree sensor 70 outputs a signal relating to the opening degree of the throttle valve 8 (see FIG. 2). The air flow meter 71 is provided on the air cleaner and outputs a signal relating to the flow rate of intake air. The crank angle sensor 72 outputs a signal relating to a rotation speed of a crankshaft (not illustrated), that is, an engine rotation speed.

The intake air oxygen concentration sensor 73 outputs a signal relating to oxygen concentration contained in intake air and the temperature of the intake air oxygen concentration sensor 73. The intake air oxygen concentration sensor 73 includes a sensor element 73a detecting oxygen concentration and an electric heater 73b heating the sensor element 73a.

Electric power is supplied to the electric heater 73b from, for example, a battery (not illustrated). Electric power, which is generated by a generator (not illustrated) capable of being driven using, for example, a portion of a driving power of the engine 1, is supplied to the battery and the battery is charged.

The temperature of the sensor element 73a is raised to be greater than or equal to the activation temperature so as to make it possible for the intake air oxygen concentration sensor 73 to enter an active state in which oxygen concentration can be accurately detected. The electric heater 73b is embedded in the sensor element 73a.

A conduction duty ratio to the electric heater 73b is controlled so as to make it possible to control the temperature of the sensor element 73a, that is, the temperature of the intake air oxygen concentration sensor 73.

In a case where the temperature of the intake air oxygen concentration sensor 73 is controlled, first, impedance of the sensor element 73a is detected as a parameter relating to the temperature of the sensor element 73a. The conduction duty ratio to the electric heater 73b is controlled based on a difference between target impedance corresponding to a target temperature of the sensor element 73a and actual impedance corresponding to an actual temperature of the sensor element 73a. With this, the temperature of the intake air oxygen concentration sensor 73 is controlled. The higher the temperature of the sensor element 73a, impedance of the sensor element 73a becomes lower.

The ECU 50 includes a rotation speed detection unit 51, an idle-ON determination unit 52, a fuel cut determination unit (in the following, referred to as an FC determination unit) 53, a load rate calculation unit 54, a target EGR rate setting unit 55, an impedance setting unit 56, an impedance detection unit 57, an oxygen concentration detection unit 58, an EGR rate calculation unit 59, an EGR rate feedback execution determination unit (in the following, referred to as an EGR rate FB execution determination unit) 60, a heater control unit 61, and a valve control unit 62.

The ECU 50 includes a central processing unit (CPU), a read only memory (ROM), a random access memory (RAM), an input and output (I/O) port, an AD conversion unit, and the like, and these components are connected with each other through a bus.

The CPU reads a program stored in the ROM and executes the program by using the RAM as a working area. With this, the ECU 50 functions as the rotation speed detection unit 51, the idle-ON determination unit 52, the heater control unit 61, the valve control unit 62, and the like. It is possible to configure at least some or all of respective components with only hardware. The respective components may be integrated or divided. The ECU 50 may be configured with a plurality of control units.

The rotation speed detection unit 51 detects the engine rotation speed based on the signal from the crank angle sensor 72.

The idle-ON determination unit 52 determines whether a state of the engine 1 is in an idle-ON state at which an accelerator pedal (not illustrated) is not depressed or not, based on the signal from the throttle opening degree sensor 70. In a case where the accelerator pedal is not depressed by a driver, the opening degree of the throttle valve 8 is in a predetermined low opening degree. Accordingly, in a case where the opening degree of the throttle valve 8 is in the predetermined low opening degree, the idle-ON determination unit 52 determines that the state of the engine 1 is an idle-ON state.

The FC determination unit 53 determines whether the state of the engine 1 is a fuel cut state, at which fuel cut that causes stop of fuel injection during travelling is executed, or not, based on the determination result by the idle-ON determination unit 52 and the engine rotation speed detected by the rotation speed detection unit 51. The fuel cut is executed in a case where the state of the engine 1 is the idle-ON state and the engine rotation speed is greater than a predetermined rotation speed. The predetermined rotation speed is a preset rotation speed, a lower limit rotation speed at which the fuel cut is executed, and is greater than an idle rotation speed.

In a case where the state of the engine 1 is the idle-ON state and the engine rotation speed is greater than the predetermined rotation speed, the FC determination unit 53 determines that the state of the engine 1 is a fuel cut state.

In a case where the state of the engine 1 is not the idle-ON state and the engine rotation speed is less than or equal to the predetermined rotation speed, the FC determination unit 53 determines that the state of the engine 1 is not the fuel cut state.

The fuel cut is not limited to the conditions described above and may be executed or stopped in consideration of condition such as the temperature of cooling water which cools down the engine 1. In this case, the FC determination unit 53 determines whether the state of the engine 1 is the fuel cut state or not, according to respective conditions.

The load rate calculation unit 54 detects an intake flow rate based on the signal from the air flow meter 71 and calculates an engine load rate based on the intake flow rate. The load rate calculation unit 54 calculates the engine load rate by dividing an intake air amount, which is an amount of intake air sucked into the cylinder 2 (combustion chamber), for example, when one combustion cycle is performed, in the engine 1 by capacity of the cylinder 2.

The impedance setting unit 56 sets target impedance based on the engine load rate calculated by the load rate calculation unit 54, the engine rotation speed detected by the rotation speed detection unit 51, and the determination result of the idle-ON determination unit 52.

Specifically, in a case where the state of the engine 1 is the idle-ON state, the impedance setting unit 56 sets target impedance to impedance of the sensor element 73a in a case where the electric heater 73b is turned OFF and is not heated by the electric heater 73b. The impedance setting unit 56 sets, for example, target impedance to impedance of the sensor element 73a in a case of being not influenced by heating by the electric heater 73b. In the following impedance which is set is referred to as an "OFF value". The OFF value is a value for turning the electric heater 73b OFF.

In the idle-ON state, EGR gas is not recirculated and thus, oxygen concentration does not need to be detected by the intake air oxygen concentration sensor 73. For that reason, in a case of the idle-ON state, target impedance is set to the OFF value in order to turn the electric heater 73b OFF. With this, it is possible to reduce power consumption of the electric heater 73b.

In a case where the state of the engine 1 is not the idle-ON state, the impedance setting unit 56 sets target impedance based on the engine load rate and the operation state of the engine determined by the engine rotation speed.

Figure 4:
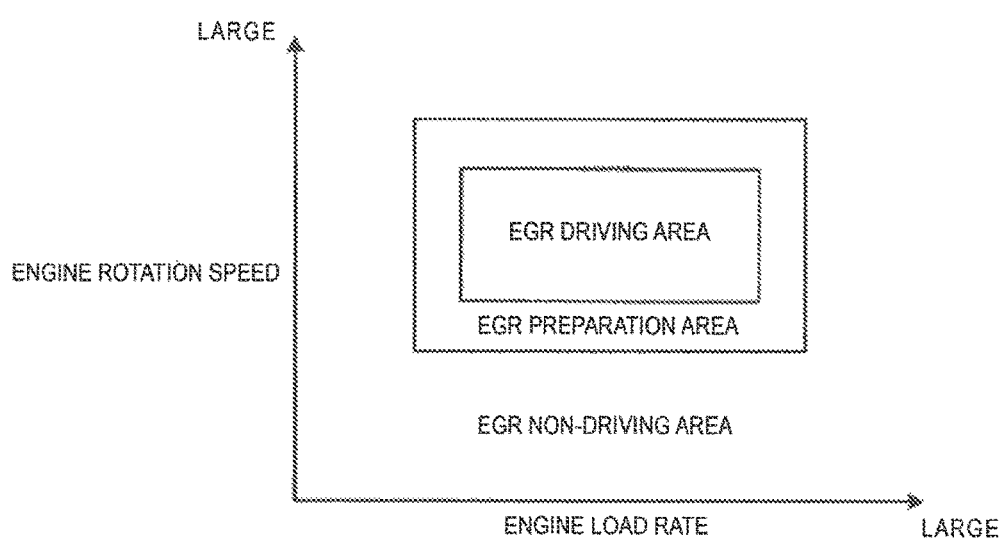
FIG. 4 is a map illustrating a relationship between an engine load rate, an engine rotation speed, and an engine operation state.

In this case, the impedance setting unit 56, first, determines in which area of the EGR driving area, the EGR preparation area, and the EGR non-driving area the operation state of the engine 1 is present, based on a map illustrated in FIG. 4. FIG. 4 is a map illustrating a relationship between the engine load rate, the engine rotation speed, and the operation state of the engine 1. In actual, the EGR driving area and the EGR preparation area are not areas surrounded by straight lines, but illustrated as rectangular areas surrounded by straight lines in FIG. 4 in order to explain the EGR driving area and the EGR preparation area.

The impedance setting unit 56 sets target impedance according to the operation state of the engine 1.

In a case where the operation state of the engine 1 is in the EGR driving area, the impedance setting unit 56 sets the target temperature to a temperature higher than the activation temperature, for example, 750 degrees in order to put the intake air oxygen concentration sensor 73 into the active state and sets target impedance to a base active value corresponding to the target temperature. When actual impedance of the sensor element 73a becomes the base active value, it is possible to determine that the intake air oxygen concentration sensor 73 is maintained at a temperature higher than the activation temperature and the intake air oxygen concentration sensor 73 is stable in the active state. The base active value is a value with which it is possible to determine that the intake air oxygen concentration sensor 73 is stable in the active state.

In a case where the operation state of the engine 1 is in the EGR preparation area and is not in learning during which the opening degree of the EGR valve 22 is learned, the impedance setting unit 56 sets a target temperature to a temperature, which is lower than the activation temperature and higher than the inactivation temperature, for example, 650 degrees and sets target impedance to a semi-active value corresponding to the target temperature in order to put the intake air oxygen concentration sensor 73 into the semi-active state. Learning of the opening degree of the EGR valve 22 will be described later.

In a case where the operation state of the engine 1 transited from the EGR preparation area to the EGR driving area, the semi-active value is a value corresponding to a temperature with which the temperature of the intake air oxygen concentration sensor 73 is capable of being quickly raised to be greater than or equal to the activation temperature.

In a case where the operation state of the engine 1 is in the EGR preparation area and is not in learning during which the opening degree of the EGR valve 22 is learned, the intake air oxygen concentration sensor 73 is put into the semi-active state so as to make it possible to reduce power consumption of the electric heater 73b than in a case where the intake air oxygen concentration sensor 73 is maintained in the active state. In a case where the operation state of the engine 1 transited from the EGR preparation area to the EGR driving area, it is possible to quickly put the intake air oxygen concentration sensor 73 into the active state.

In a case where the operation state of the engine 1 is in the EGR preparation area and is in learning during which the opening degree of the EGR valve 22 is learned, the impedance setting unit 56 sets target impedance to the base active value in order to put the intake air oxygen concentration sensor 73 into the base active state. As such, although details will be described later, target impedance is set to the base active value so as to make it possible to quickly complete learning of the opening degree of the EGR valve 22.

In a case where the operation state of the engine 1 is in the EGR non-driving area, the impedance setting unit 56 sets target impedance to the OFF value in order to turn the electric heater 73b OFF and put the intake air oxygen concentration sensor 73 into the inactive state, similarly to the case of the idle-ON state. With this, it is possible to reduce power consumption of the electric heater 73b.

The impedance detection unit 57 detects actual impedance, which is current impedance of the sensor element 73a, from the signal of the intake air oxygen concentration sensor 73.

The heater control unit 61 includes a heater output setting unit 61a and a heater output unit 61b.

The heater output setting unit 61a sets a conduction duty ratio to the electric heater 73b based on target impedance set by the impedance setting unit 56 and actual impedance detected by the impedance detection unit 57.

Specifically, the heater output setting unit 61a executes feedback control based on target impedance and actual impedance and sets the conduction duty ratio. The smaller target impedance, that is, the higher the target temperature, the conduction duty ratio is set so that a percentage of ON per a unit time is increased. In a case where target impedance is the OFF value, the percentage of ON in the conduction duty ratio is zero.

The heater output unit 61b outputs the conduction duty ratio set by the heater output setting unit 61a to the electric heater 73b, controls the temperature of the sensor element 73a by the electric heater 73b, and controls the temperature of the intake air oxygen concentration sensor 73.

The target EGR rate setting unit 55 sets the target EGR rate based on the operation state of the engine 1. Specifically, in a case where the operation state of the engine 1 is in the EGR preparation area or the EGR non-driving area, the target EGR rate setting unit 55 sets the target EGR rate to zero such that EGR gas is not recirculated to the intake pipe 3.

In a case where the operation state of the engine 1 is in the EGR driving area, the target EGR rate setting unit 55 sets a target EGR rate according to respective operation states of the engine 1. A plurality of values are set as the target EGR rate and the target EGR rate setting unit 55 sets the target EGR rate according to respective operation states of the engine 1.

In a case where the operation state of the engine 1 is in the EGR driving area, the EGR rate FB execution determination unit 60 determines whether EGR rate feedback control (in the following, referred to as EGR rate FB control) is to be executed or not, based on an absolute value of a difference between target impedance and actual impedance. In EGR rate FB control, the opening degree of the EGR valve 22 is feedback-controlled based on the target EGR rate and the actual EGR rate.

In a case where the operation state of the engine 1 is in the EGR driving area and the absolute value of the difference between target impedance and actual impedance is less than or equal to a predetermined value, the EGR rate FB execution determination unit 60 determines that the EGR rate FB control is to be executed. The predetermined value is a preset value with which the temperature of the intake air oxygen concentration sensor 73 becomes sufficiently high and it is possible to determine that the intake air oxygen concentration sensor 73 is stable in the active state.

In a case where the operation state of the engine 1 is in the EGR driving area and the absolute value of the difference between target impedance and actual impedance is greater than the predetermined value, the EGR rate FB execution determination unit 60 determines that the EGR rate FB control is not to be executed.

In the case where the absolute value of the difference between target impedance and actual impedance is greater than the predetermined value, the temperature of the intake air oxygen concentration sensor 73 does not become sufficiently high and the intake air oxygen concentration sensor 73 is not stable in the active state.

In such a state, when the EGR rate FB control is executed, there is a concern that the actual EGR rate does not become the target EGR rate and fuel consumption is deteriorated. For that reason, in a case where the intake air oxygen concentration sensor 73 is not stable in the active state, although details will be described later, the opening degree of the EGR valve 22 is not set by the EGR rate FB control and the opening degree of the EGR valve 22 is set to a predetermined opening degree.

The oxygen concentration detection unit 58 detects oxygen concentration of intake air based on the signal from the intake air oxygen concentration sensor 73.

The EGR rate calculation unit 59 calculates the actual EGR rate based on oxygen concentration of intake air detected by the oxygen concentration detection unit 58. The EGR rate calculation unit 59 calculates the actual EGR rate by dividing a difference between oxygen concentration of intake air and oxygen concentration of fresh air (atmospheric air) by oxygen concentration of fresh air. Oxygen concentration of fresh air is a preset value.

The valve control unit 62 includes a learning unit 62a, an opening degree setting unit 62b, and a valve opening degree output unit 62c.

The learning unit 62a learns a predetermined opening degree of the EGR valve 22 in order to correct a tolerance of the EGR valve 22 and deviation in an actual EGR rate caused by aging deterioration, that is, deviation in the opening degree of the EGR valve 22, with respect to the target EGR rate. The predetermined opening degree is set according to the target EGR rate and an initial value of the predetermined opening degree is set in advance according to each target EGR rate. Learning is performed so as to cause the predetermined opening degree according to each target EGR rate to be updated.

When an update condition is satisfied, the learning unit 62a determines that the predetermined opening degree of the EGR valve 22 is to be updated and starts learning.

The update condition corresponds to, for example, a case where a traveling distance becomes a predetermined distance which is set in advance or a case where the time during which the actual EGR rate converges into the target EGR rate becomes longer than a predetermined time which is set in advance. A plurality of the predetermined distances are set so that learning is performed a plurality of times. When only the update condition is satisfied, it enters a state where the opening degree of the EGR valve 22 is being learned.

When a learning condition is satisfied during learning, the learning unit 62a updates the predetermined opening degree of the EGR valve 22 and completes learning.

The learning condition is, for example, matter that the intake air oxygen concentration sensor 73 is stable in the active state, matter that the operation state of the engine 1 is in an area which becomes a predetermined target EGR rate of the EGR driving area, and the timing at which the actual EGR rate becomes the predetermined target EGR rate. The predetermined target EGR rate is a preset value. A plurality of the predetermined target EGR rates may be set in the EGR driving area. Learning is performed under the same condition so as to make it possible to accurately perform learning of the predetermined opening degree.

In a case where the learning condition is satisfied, the learning unit 62a updates the predetermined opening degree of the EGR valve 22 based on the opening degree of the EGR valve 22 in a case where the actual EGR rate becomes the predetermined target EGR rate.

The learning unit 62a updates the predetermined opening degrees of the EGR valve 22 corresponding to respective target EGR rates, respectively, based on the predetermined opening degrees of the EGR valve 22, in the updated predetermined target EGR rates.

The opening degree setting unit 62b sets the opening degree of the EGR valve 22 based on the target EGR rate set by the target EGR rate setting unit 55, the actual EGR rate calculated by the EGR rate calculation unit 59, the determination result by the EGR rate FB execution determination unit 60, and the determination result by the FC determination unit 53.

In a case of the fuel cut state, the opening degree setting unit 62b maximizes the opening degree of the EGR valve 22 and fully opens the EGR valve 22. In a case where the fuel cut is executed, it is possible to prevent the temperature of the intake air oxygen concentration sensor 73 from being reduced by opening the EGR valve 22 fully and increasing the recirculation amount of EGR gas, which is a portion of exhaust gas after passing through the ternary catalyst device 10 (see FIG. 2). In making the EGR valve 22 open fully, setting of the opening degree of the EGR valve 22 to an opening degree in the vicinity of full-open is included.

In a case where the operation state of the engine 1 is in the EGR driving area and it is determined that EGR rate FB control is not to be executed by the EGR rate FB execution determination unit 60, the opening degree setting unit 62b sets the opening degree of the EGR valve 22 to the predetermined opening degree according to the target EGR rate.

In a case where the operation state of the engine 1 is in the EGR driving area and it is determined that EGR rate FB control is to be executed by the EGR rate FB execution determination unit 60, the opening degree setting unit 62b sets the opening degree of the EGR valve 22 by EGR rate FB control so that the actual EGR rate becomes the target EGR rate.

Even in a case where the opening degree of the EGR valve 22 is set to the predetermined opening degree according to the target EGR rate, the actual EGR rate may not coincide with the target EGR rate according to the operation state of the engine 1.

When the absolute value of the difference between target impedance and actual impedance becomes less than or equal to the predetermined value and the intake air oxygen concentration sensor 73 is stable in the active state, the opening degree setting unit 62b sets the opening degree of the EGR valve 22 by feedback control so that the actual EGR rate becomes the target EGR rate. With this, it is possible to accurately control the flow rate of EGR gas by using the actual EGR rate as the target EGR rate and it is possible to put a combustion state into a state intended to be a target. For that reason, it is possible to improve fuel consumption.

The valve opening degree output unit 62c outputs a control signal of the EGR valve 22 so that the opening degree of the EGR valve 22 becomes the opening degree set by the opening degree setting unit 62b, and controls the opening degree of the EGR valve 22.

4. Electric Heater Output Control

Figure 5:
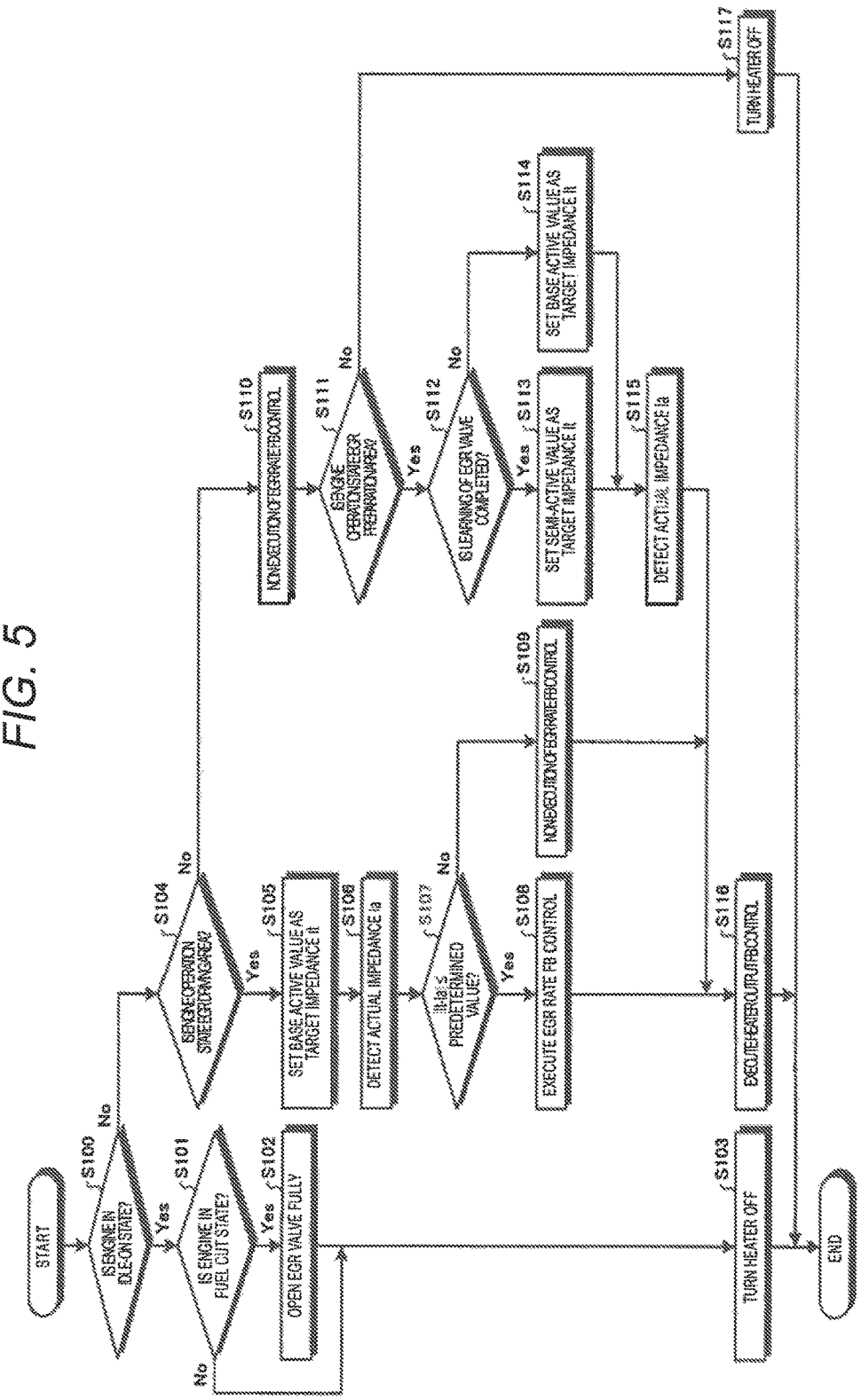
FIG. 5 is a flowchart for explaining output control of the electric heater.

Next, description will be made on output control of the electric heater 73b with reference to a flowchart of FIG. 5. FIG. 5 is a flowchart for explaining output control of the electric heater 73b.

In Step S100, the idle-ON determination unit 52 determines whether the state of the engine 1 is in the idle-ON state or not. In a case where the state of the engine 1 is in the idle-ON state, processing proceeds to Step S101 and in a case where the state of the engine 1 is not in the idle-ON state, processing proceeds to Step S104.

In Step S101, the FC determination unit 53 determines whether the state of the engine 1 is in the fuel cut state or not. In a case where the state of the engine 1 is in the fuel cut state, processing proceeds to Step S102 and in a case where the state of the engine 1 is not in the fuel cut state, processing proceeds to Step S103.

In Step S102, the valve control unit 62 maximizes the opening degree of the EGR valve 22 and fully opens the EGR valve 22.

In Step S103, the heater control unit 61 turns the electric heater 73b OFF.

In Step S104, the impedance setting unit 56 determines whether the operation state of the engine 1 is in the EGR driving area or not. In a case where the operation state of the engine 1 is in the EGR driving area, processing proceeds to Step S105. In a case where the operation state of the engine 1 is in the EGR preparation area or the EGR non-driving area, processing proceeds to Step S110.

In Step S105, the impedance setting unit 56 sets target impedance (It) to the base active value.

In Step S106, the impedance detection unit 57 detects actual impedance (Ia).

In Step S107, the EGR rate FB execution determination unit 60 calculates the absolute value of difference between target impedance (It) and the actual impedance (Ia) and determines whether the calculated absolute value is less than or equal to the predetermined value or not. In a case where the calculated absolute value is less than or equal to the predetermined value, processing proceeds to Step S108, and in a case where the calculated absolute value is greater than the predetermined value, processing proceeds to Step S109.

In Step S108, the target EGR rate setting unit 55 sets the target EGR rate and the EGR rate calculation unit 59 calculates the actual EGR rate. The valve control unit 62 executes EGR rate FB control and controls the opening degree of the EGR valve 22.

In Step S109, the target EGR rate setting unit 55 sets the target EGR rate. The valve control unit 62 does not execute EGR rate FB control, sets the opening degree of the EGR valve 22 to the predetermined opening degree according to the target EGR rate, and controls the opening degree of the EGR valve 22.

In Step S110, since the operation state of the engine 1 is not in the EGR driving area, the valve control unit 62 ends EGR rate FB control in a case where EGR rate FB control is being executed.

In Step S111, the impedance setting unit 56 determines whether the operation state of the engine 1 is in the EGR preparation area or not. In a case where the operation state of the engine 1 is in the EGR preparation area, processing proceeds to Step S112 and in a case where the operation state of the engine 1 is not in the EGR preparation area, that is, in a case where the operation state of the engine 1 is in the EGR non-driving area, processing proceeds to Step S117.

In Step S112, the valve control unit 62 determines whether learning of the opening degree of the EGR valve 22 is completed or not. Specifically, the valve control unit 62 determines whether the learning condition is satisfied after the update condition is satisfied and the predetermined opening degree of the EGR valve 22 is updated or not. In a case where the predetermined opening degree of the EGR valve 22 is updated after the update condition is satisfied, the opening degree of the EGR valve 22 is not being learned, and learning of the opening degree of the EGR valve 22 is completed, processing proceeds to Step S113. On the other hand, in a case where the predetermined opening degree of the EGR valve 22 is not updated after the update condition is satisfied, the opening degree of the EGR valve 22 is being learned, and learning of the opening degree of the EGR valve 22 is not completed, processing proceeds to Step S114.

In Step S113, the impedance setting unit 56 sets target impedance (It) to the semi-active value.

In Step S114, the impedance setting unit 56 sets target impedance (It) to the base active value.

In Step S115, the impedance detection unit 57 detects actual impedance (Ia).

In Step S116, the heater control unit 61 sets the conduction duty ratio to the electric heater 73b so that actual impedance (Ia) becomes the target impedance (It), executes feedback control, and controls the temperature of the intake air oxygen concentration sensor 73 by the electric heater 73b.

In Step S117, the heater control unit 61 turns the electric heater 73b OFF.

Next, description will be made on output control of the electric heater 73b with reference to a time chart of FIG. 6. FIG. 6 is a time chart for explaining output control of the electric heater 73b.

Here, it is assumed that learning by the learning unit 62a is not being performed and the predetermined opening degree of the EGR valve 22 is updated. In order to explain the predetermined opening degree of the EGR valve 22 before update, the opening degree of the EGR valve 22 is illustrated by a dotted line. Description will be simply made by using an EGR rate by regarding that the actual EGR rate is not delayed with respect to the target EGR rate and deviation or the like does not occur.

Before time t0, the operation state of the engine 1 is in the EGR driving area, is maintained at a fixed state, the EGR rate is also maintained at a fixed value. Target impedance and actual impedance have base active values.

At the time t0, for example, the engine load rate is small and accordingly, the operation state of the engine 1 is changed from the EGR driving area toward the EGR preparation area. The operation state of the engine 1 is changed such that the EGR rate becomes small. For that reason, the opening degree of the EGR valve 22 becomes small.

At time t1, when the operation state of the engine 1 enters a state of being in the EGR preparation area, EGR gas is not recirculated and thus, the EGR rate becomes zero, the opening degree of the EGR valve 22 becomes zero, that is, the EGR valve 22 is fully closed. In order to put the intake air oxygen concentration sensor 73 into the semi-active state, target impedance is set to the semi-active value which is greater than the base active value. With this, the conduction duty ratio of the electric heater 73b becomes small, the heating amount by the electric heater 73b becomes small and thus, the temperature of the intake air oxygen concentration sensor 73 is lowered and actual impedance is gradually increased.

At time t2, when the state of the engine 1 enters the fuel cut state and the operation state of the engine 1 becomes a state of being in the EGR non-driving area, target impedance is set to the OFF value in order to put the intake air oxygen concentration sensor 73 into the inactive state. For that reason, the conduction duty ratio of the electric heater 73b becomes zero and the electric heater 73b becomes OFF. The opening degree of the EGR valve 22 becomes the maximum opening degree, that is, the EGR valve 22 is fully opened and EGR gas is recirculated.

A conduction duty ratio of a comparative example in which the intake air oxygen concentration sensor 73 is in the active state at all times regardless of the operation state of the engine 1 is illustrated by a dotted line. In the embodiment, the intake air oxygen concentration sensor 73 is put into the semi-active state or the inactive state according to the operation state of the engine 1 so as to make it possible to further reduce power consumption of the electric heater 73b than that in the comparative example.

Change in actual impedance, that is, the temperature of the intake air oxygen concentration sensor 73 of the comparative example, in which the EGR valve 22 is not opened and EGR gas is not recirculated at the time t2, is illustrated by a two-dotted line in and after the time t2.

In the comparative example, EGR gas is not recirculated and thus, the temperature of the intake air oxygen concentration sensor 73 becomes lower than that of the intake air oxygen concentration sensor 73 of the embodiment and actual impedance of the comparative example becomes greater that actual impedance of the embodiment.

At time t3, for example, when the accelerator pedal is depressed, the fuel cut is ended and the opening degree of the EGR valve 22 becomes zero. The operation state of the engine 1 is in the EGR non-driving area.

At time t4, when the operation state of the engine 1 enters in a state of being in the EGR preparation area, in order to put the intake air oxygen concentration sensor 73 into the semi-active state, the target impedance is set to the semi-active value to increase the conduction duty ratio of the electric heater 73b. With this, the sensor element 73a of the intake air oxygen concentration sensor 73 is heated by the electric heater 73b and the actual impedance becomes small.

At time t5, when the operation state of the engine 1 enters in a state of being in the EGR driving area, the opening degree of the EGR valve 22 becomes large according to the operation state of the engine 1 to increase the EGR rate. In order to put the intake air oxygen concentration sensor 73 into the active state, the target impedance is set to the base active value and the conduction duty ratio of the electric heater 73b is increased. With this, the sensor element 73a of the intake air oxygen concentration sensor 73 is heated by the electric heater 73b and the actual impedance becomes small.

Here, the absolute value of the difference between the target impedance and the actual impedance is greater than the predetermined value and EGR rate FB control is not executed.

At time t6, when the absolute value of the difference between target impedance and actual impedance becomes less than or equal to the predetermined value, EGR rate FB control is executed.

In the comparative example, EGR gas is not recirculated while the fuel cut is performed and thus, the temperature of the intake air oxygen concentration sensor 73 is lowered during performance of the fuel cut. For that reason, thereafter, in a case where the operation state of the engine 1 enters in a state of being in the EGR driving area, the time until the absolute value of the difference between target impedance and actual impedance becomes less than or equal to the predetermined value becomes long, the absolute value becomes less than or equal to the predetermined value at time t7, and EGR rate FB control is executed at the time t7. In the comparative example, a state of EGR rate FB control is illustrated by a dotted line.

In the embodiment, when it enters the fuel cut state, the EGR valve 22 is fully opened, thereafter, so as to make it is possible to quickly start EGR rate FB control than in the comparative example and to improve fuel consumption, in a case where the operation state of the engine 1 enters in a state of being in the EGR driving area.

5. Effects

The conduction duty ratio of the electric heater 73b is controlled so that the intake air oxygen concentration sensor 73 enters any of an active state where a temperature of the intake air oxygen concentration sensor becomes greater than or equal to an activation temperature, a semi-active state where the temperature is lower than that in the active state, and an inactive state where the temperature is lower than that in the semi-active state according to the operation state of the engine 1. With this, it is possible to reduce power consumption of the electric heater 73b compared to a case where the intake air oxygen concentration sensor 73 is heated by the electric heater 73b so as to be maintained at the active state at all times.

Power consumption of the electric heater 73b is reduced so as to make it possible to shorten a driving time of a generator driven using a portion of a driving power of the engine 1 and improve fuel consumption of the engine 1.

In a case where the operation state of the engine 1 is in the idle-ON state, the electric heater 73b is turned OFF so that the intake air oxygen concentration sensor 73 enters the inactive state. With this, it is possible to reduce power consumption of the electric heater 73b. Also, it is possible to improve fuel consumption of the engine 1.

In a case where the fuel cut is executed, the EGR valve 22 is opened fully so as to make it possible to recirculate EGR gas of which the temperature is higher than that of fresh air and prevent the temperature of the intake air oxygen concentration sensor 73 from being reduced. With this, thereafter, when the intake air oxygen concentration sensor 73 is intended to be set to the active state, it is possible for the intake air oxygen concentration sensor 73 to be put from state where the temperature of the intake air oxygen concentration sensor 73 is high to the active state and it is possible to reduce power consumption of the electric heater 73b and improve fuel consumption of the engine 1. In a case where the operation state of the engine 1 became the EGR driving area, it is possible for the intake air oxygen concentration sensor 73 to be quickly put into the active state, and it is possible to quickly start EGR rate FB control and improve fuel consumption of the engine 1.

In a case where the operation state of the engine 1 is in the EGR non-driving area, the electric heater 73b is turned OFF so that the intake air oxygen concentration sensor 73 enters the inactive state. With this, it is possible to reduce power consumption of the electric heater 73b. Also, it is possible to improve fuel consumption of the engine 1.

In a case where the operation state of the engine 1 is in the EGR preparation area, the conduction duty ratio of the electric heater 73b is controlled so that the intake air oxygen concentration sensor 73 enters the semi-active state. With this, in a case where the operation state of the engine 1 becomes the EGR driving area, it is possible for the intake air oxygen concentration sensor 73 to be quickly put into the active state while reducing power consumption of the electric heater 73b, and it is possible to quickly start EGR rate FB control and improve fuel consumption of the engine 1.

In a case where the opening degree of the EGR valve 22 is not being learned and the operation state of the engine 1 is in the EGR preparation area, the conduction duty ratio of the electric heater 73b is controlled so that the intake air oxygen concentration sensor 73 enters the semi-active state. With this, in a case where the operation state of the engine 1 enters the EGR driving area, it is possible for the intake air oxygen concentration sensor 73 to be quickly put into the active state while reducing power consumption of the electric heater 73b, and it is possible to quickly start EGR rate FB control and improve fuel consumption of the engine 1.

In a case the opening degree of the EGR valve 22 is being learned and the operation state of the engine 1 is in the EGR preparation area, the conduction duty ratio of the electric heater 73b is controlled so that the intake air oxygen concentration sensor 73 enters the active state. With this, when the operation state of the engine 1 is changed from the EGR preparation area to the EGR driving area, the temperature of the intake air oxygen concentration sensor 73 is already in the active state, and thus, it is possible to quickly perform learning of the opening degree of the EGR valve 22.

6. Modified Example

Although in the embodiment, the EGR gas recirculation pipe 21 is connected to the exhaust pipe 4 between the ternary catalyst device 10 and NOx occlusion and reduction type ternary catalyst device 11, the EGR gas recirculation pipe 21 may be connected to the exhaust pipe 4 between the cylinder 2 and the ternary catalyst device 10.

The engine 1 may include a supercharger such as a turbo supercharger and output control of the electric heater 73b of the embodiment described above may be applied to the engine 1 including the supercharger.

In a case where the EGR valve 22 is fully opened in the fuel cut state and EGR gas is recirculated, cooling of EGR gas by the EGR cooler 23 (see FIG. 2) may be reduced or EGR gas may be recirculated without being cooled down.

With this, when the temperature of the intake air oxygen concentration sensor 73 is prevented from being reduced, the operation state of the engine 1 is in the EGR driving area, and the intake air oxygen concentration sensor 73 is put into the active state, it is possible for the intake air oxygen concentration sensor 73 to be put from the state where the temperature of the intake air oxygen concentration sensor 73 is high to the active state and it is possible to reduce power consumption of the electric heater 73b. It is possible for the intake air oxygen concentration sensor 73 to be quickly put into the active state, and it is possible to quickly start EGR rate FB control and improve fuel consumption of the engine 1.

Further effects and a modification example may be easily derived by a person having ordinary skill in the art. For that reason, a broader aspect of the present invention is not limited to specific details and representative embodiments as having been described above. Accordingly, various changes may be made without departing from a spirit or a scope of a general inventive concept defined by attached claims and equivalents thereof.

What is claimed is:

1. An engine control device of an engine of a vehicle, the engine control device comprising a processor configured to:
   detect an operation state of the engine; and
   control an output of a heater which heats an intake air oxygen concentration sensor detecting oxygen concentration of intake air of the engine, the intake air including a portion of exhaust gas recirculated to an intake passage of the engine as EGR gas,
   wherein the processor controls the output of the heater, according to the operation state of the engine detected by the processor, so that the intake air oxygen concentration sensor enters one of (i) an active state where a temperature of the intake air oxygen concentration sensor becomes greater than or equal to an activation temperature, (ii) a semi-active state where the temperature of the intake air oxygen concentration sensor is lower than the activation temperature and higher than an inactivation temperature, and (iii) an inactive state where the temperature is lower than the inactivation temperature, and
   wherein in a case where the operation state of the engine is in an EGR preparation area which is a transition area between an EGR driving area, in which the EGR gas is allowed to be recirculated to the intake passage, and an EGR non-driving area, the processor controls the output of the heater so that the intake air oxygen concentration sensor enters the semi-active state.

2. The engine control device according to claim 1, wherein
   in a case where an accelerator pedal of the vehicle is not depressed, the processor turns the heater OFF so that the intake air oxygen concentration sensor enters the inactive state.

3. The engine control device according to claim 1, wherein
the processor is further configured to fully open an EGR valve provided in an EGR passage of the engine, which allows the EGR gas to be recirculated to the intake passage, in a case where fuel cut is executed stopping a fuel injection to the engine during travelling of the vehicle.

4. The engine control device according to claim 1, wherein
in a case where the operation state of the engine is in an EGR non-driving area in which the EGR gas is not allowed to be recirculated to the intake passage, the processor turns the heater OFF so that the intake air oxygen concentration sensor enters the inactive state.

5. The engine control device according to claim 1, wherein
the processor is further configured to learn an opening degree of an EGR valve provided in an EGR passage, which allows the EGR gas to be recirculated to the intake passage, based on the oxygen concentration of the intake air detected by the intake air oxygen concentration sensor,
in a case where the opening degree of the EGR valve is not being learned and the operation state of the engine is in the EGR preparation area, the processor controls the output of the heater so that the intake air oxygen concentration sensor enters the semi-active state, and
in a case where the opening degree of the EGR valve is being learned and the operation state of the engine is in the EGR preparation area, the processor controls the output of the heater so that the intake air oxygen concentration sensor enters the active state.

* * * * *